(12) United States Patent
Cho et al.

(10) Patent No.: US 6,210,426 B1
(45) Date of Patent: Apr. 3, 2001

(54) OPTICAL RADIATION TREATMENT FOR PREVENTION OF SURGICAL SCARS

(75) Inventors: George Cho, Hopkinton; Horace Furumoto, Wellesley; Rafael A Sierra, Palmer, all of MA (US)

(73) Assignee: Cynosure Inc, Chelmsford, MA (US)

( * ) Notice: Subject to any disclaimer, the term of this patent is extended or adjusted under 35 U.S.C. 154(b) by 0 days.

(21) Appl. No.: 09/231,746

(22) Filed: Jan. 15, 1999

(51) Int. Cl.$^7$ .................................................. A61N 5/006
(52) U.S. Cl. .............................. 607/89; 606/9; 128/898
(58) Field of Search ........................... 607/88–90; 606/3, 606/9, 2; 128/395–398

(56) References Cited

U.S. PATENT DOCUMENTS

| | | | |
|---|---|---|---|
| 4,672,969 | * | 6/1987 | Dew ..................................... 128/397 |
| 5,464,436 | * | 11/1995 | Smith ..................................... 607/89 |
| 5,766,233 | * | 6/1998 | Thiberg ................................. 607/88 |
| 5,897,549 | * | 4/1999 | Tankovich .............................. 606/98 |
| 5,951,596 | * | 9/1999 | Bellinger ............................... 607/89 |
| 5,964,749 | * | 10/1999 | Eckhouse et al. ....................... 606/9 |

* cited by examiner

Primary Examiner—Linda C. M. Dvorak
Assistant Examiner—Ahmed Farah
(74) Attorney, Agent, or Firm—Don Halgren

(57) ABSTRACT

A method for the prevention of a scar on the skin of a patient after the beginning healing of a wound or surgical site on that patient. The method comprises the steps of providing an optical radiation apparatus with a handpiece communicating therewith, energizing the optical radiation apparatus to provide a beam of light, directing the light beam onto a wound or surgical site of a patient after 2 days and before 2 months from the date of injury or surgical procedure to the patient. The beam has a wavelength range of about 530 nm to 1000 nm and the beam has a fluence range of from 2 J/cm$^2$ to 12 J/cm$^2$. The beam is preferably generated by a pulsed dye laser apparatus.

10 Claims, 2 Drawing Sheets

OPTICAL RADIATION TREATMENT FOR PREVENTION OF SURGICAL SCARS

BACKGROUND OF THE INVENTION

1. Field of the Invention

This invention relates to laser treatment arrangements, and more particularly to a laser system for preventing surgical scars on human tissue.

2. Prior Art

Scars are a fact of life for most people at one time or another. Such scars may arise as a result of an accident, injury, or surgical procedure. Healing of a scar will begin immediately. The healing process may take a week to a month, depending upon the severity of the skin injury. In an injury where blood vessels are severed along with the dermis and epidermis layers of the skin, the red and white blood cells from those severed vessels leak into the wound site. The blood cells which are called platelets "thrombocytes", and a blood-clotting protein called fibrinogen, help form a clot of the blood. The cells begin to form a network, and the sides of the injury begin to join together. Cellular debris from the epidermis layer begins to invade the area amongst the blood cells. Fibroblasts, or the tissue forming cells, close in around the injury. Within twenty-four hours, the injured or clotted area becomes dehydrated, and a scab is formed at the site. Neutrophils or white blood cells travel from the blood vessels into the injured area and ingest microorganisms, cellular debris, and other foreign material. Division of the epidermal cells begins at the edge of the injury, and those cells begin to build a bridge across that tissue wound. Monocytes, or white blood cells, migrate toward the wound from its surrounding tissue.

Monocytes enter the wound site itself within two to three days after the wound or surgical procedure was created. Those monocytes ingest the remaining foreign material. The epidermal cells complete a patch of new skin under the scab that is formed. After a new epidermal surface has been formed, the protective scab is sloughed off. Then the tissue forming cells called fibroblasts begin to build scar tissue with collagen.

The epidermis has been restored after about ten days from the injury or surgical procedure, and the scab is typically gone. A tough scar tissue continues to build up, and bundles of collagen accrue along the lines of the original injury or surgical cut.

Once scars have formed, treatment of them has generally been limited to various resurfacing procedures, such as dermabrasion and chemical peels. Continuous wave carbon dioxide, argon, and pulsed dye lasers have been applied onto scar tissue in an attempt to improve the appearance of a variety of scars and keloids.

These attempts at scar treatment are performed with the attempt to ensure their removal. Such treatment is often ineffective, short-lived, and sometimes even results in additional scar formation.

It is an object of the present invention, to provide a unique wound treatment aimed at scar prevention.

It is a further object of the present invention to provide an efficient cost effective treatment for skin injuries due to accidents or surgical procedures, aimed at preventing the initial formation of scar tissue.

BRIEF SUMMARY OF THE INVENTION

The present invention comprises an arrangement for the prevention of scar formation on a wound or a surgical site. The scar prevention is accomplished by the use of an optical radiation apparatus such as a pulse dye laser. The pulse dye laser is connected to a handpiece by an elongated flexible optical fiber. The laser handpiece is supported at the distal end of the elongated flexible optical fiber and includes a lens for directing a beam of light to a surgical site or a site of an injury. The apparatus of the present invention creates a beam of light preferably having a wavelength range of between about 530 nm to about 1000 nm. The beam of optical radiation of the present invention preferably has range of pulse width between about 0.1 ms. to 10.0 ms. The fluence of the laser may extend from a range of about 2 $J/cm^2$ to about 12 $J/cm^2$. Such a laser pulse is intended to coagulate blood vessels in their initial formation stage to reduce fibroblast activity. Such reduction in fibroblast activity will minimize collagen formation to permit the injury or surgical site to have a more normal looking skin.

The method of operating the optical radiation apparatus of the present invention includes the application of the optical radiation of wavelength range between about 530 nm and 1000 nm, with a pulse width in a range of about 0.1 ms to 10.0 ms onto the situs of an injury of surgical procedure of a patient, critically within a time constraint of that injury or procedure preferably between about two days after the injury or surgical procedure has taken place, and certainly before two months of that date of injury or surgical procedure. By coagulating the blood vessels, which are typically smaller than 0.1 mm, collagen formation may be minimized and thus scar formation is also minimized or prevented. Additional treatment of the surgical site of injury may be provided by the optical radiation apparatus at follow-up intervals, preferable within that two day to two month time period from the occurrence of that injury or surgical procedure or first treatment.

Thus it has been shown that the utilization of the optical radiation apparatus with a wave length range of between about 535 nm and 1000 nm, and a fluence of about 2 $J/cm^2$ to about 12 $J/cm^2$ within a relatively short time interval after the skin injury, may minimize or prevent any scar tissue formation.

The invention thus comprises a method for the prevention of a scar on the skin of a patient after the beginning healing of a wound or surgical site, comprising the steps of providing an optical radiation apparatus with an optical radiation handpiece communicating therewith, energyzing the optical radiation apparatus, to provide a beam of light through the handpiece; and directing the beam from the handpiece onto a wound or surgical site after 2 days and before 2 months from the date of injury or surgical procedure. The method also includes the beam of light having a wavelength range of about 530 nm to about 1000 nm. The method also includes the beam having a fluence range of from 2 $J/cm^2$ to 12 $J/cm^2$. The pulsed dye laser beam also has a beam size of about 3 mm to about 10 mm in diameter.

The invention also comprises a method for the prevention of a scar on the skin of a patient after the beginning healing of a wound or surgical site, comprising the steps of: providing a pulsed dye laser apparatus with a laser handpiece communicating therewith; energyzing the pulsed dye laser apparatus to provide a beam of laser light; directing the laser beam onto a wound or surgical site after 2 days and before 2 months from the date of injury or surgical procedure, wherein the pulsed dye laser beam preferably has a wavelength range of about 575 nm to about 600 nm., the pulsed dye laser beam having a fluence range of form 2 $J/cm^2$ to 12 $J/cm^2$, the pulsed dye laser beam having a pulse width range of about 0.1 ms to 1.5 ms, and wherein the pulsed dye laser beam has a beam size range of about 3 mm to about 10 mm in diameter.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
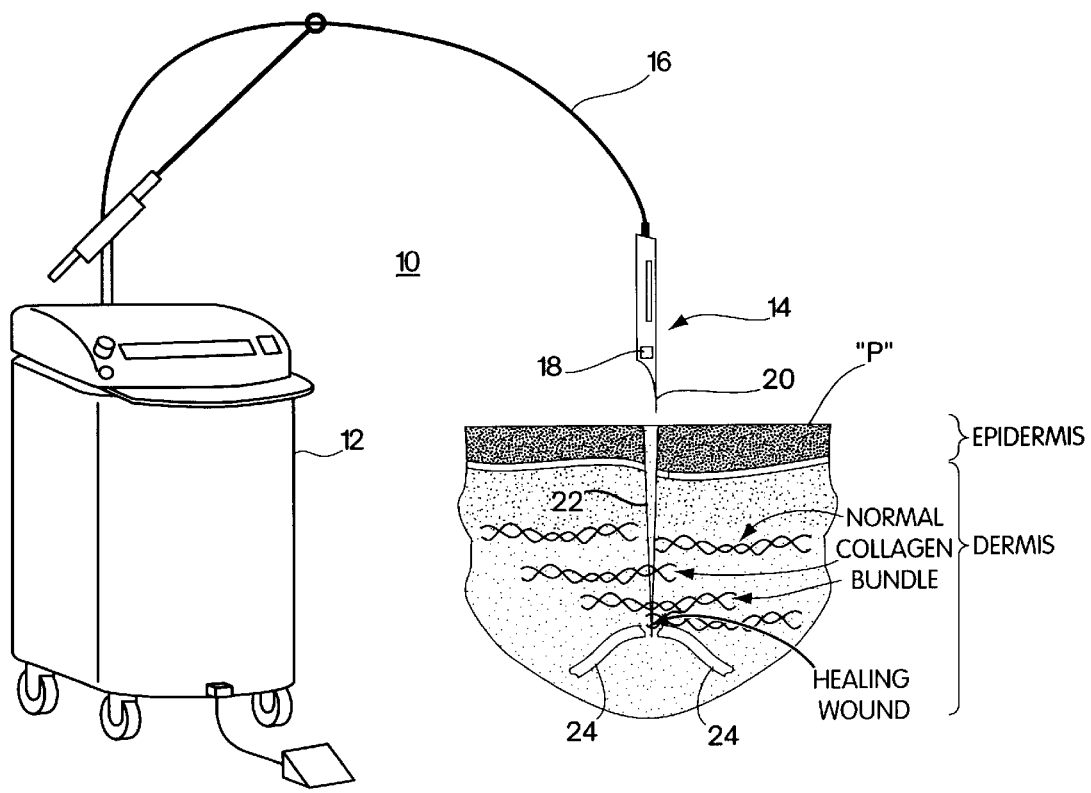
FIG. 1 is a schematic representation of an optical radiation apparatus and an appropriate handpiece directed towards a wound site on a patient, which wound site is shown in cross-section.
Figure 2D:
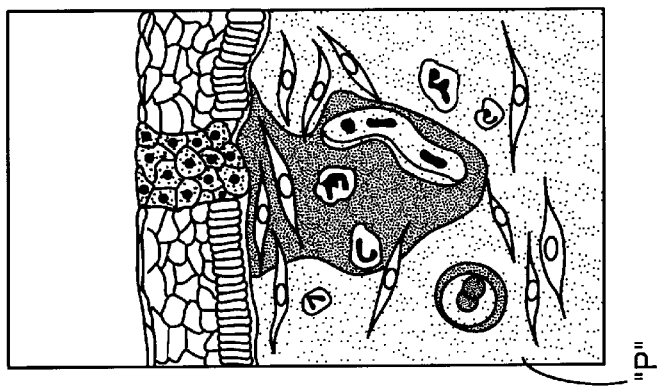
FIGS. 2 A, B, C, and D represent sectional views of a surgical or wound site-of a patient, from injury to healing of that site.
Figure 2C:
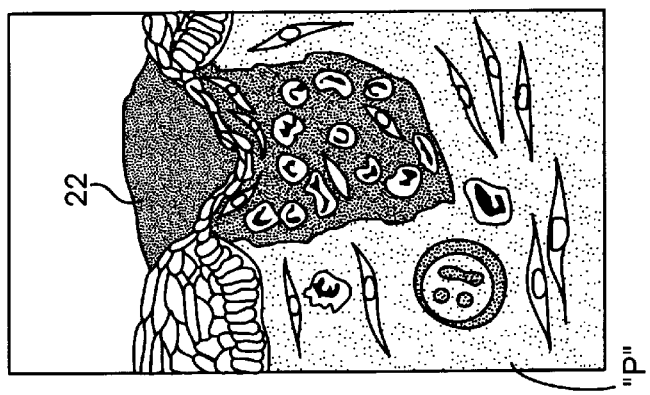
Figure 2B:
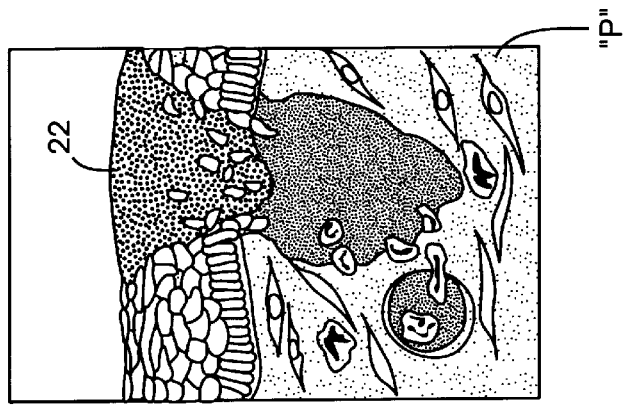
Figure 2A:
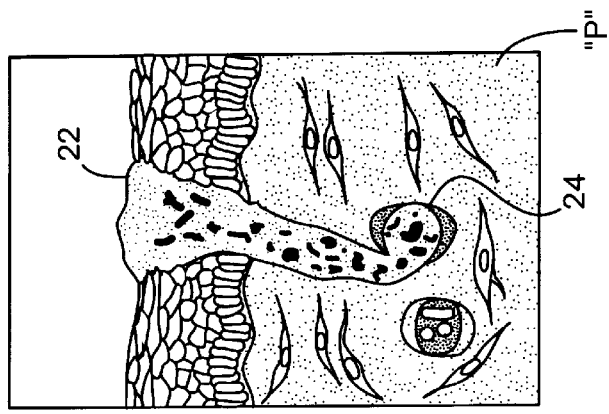

Referring now to the drawings in detail, and particularly to FIG. 1, there is shown the present invention that comprises an arrangement for the prevention of scar formation on a wound or a surgical site. The scar prevention is accomplished by the use of an optical radiation apparatus 10 such as a pulse dye laser 12. The pulse dye laser 12 is connected to a laser handpiece 14 by an elongated flexible optical fiber 16. The laser handpiece 14 is supported at the distal end of the elongated flexible optical fiber 16 includes a lens 18 for directing a beam/pulse of laser light 20 to a surgical site or a site of an injury 22 on the skin of a patient "P". The laser 12 of the present invention creates a beam of light 20 preferably having a wavelength range of about 530 nm to about 1000 nm, but preferably about 585 nm, and a beam size of about 3 mm to 10 mm in diameter. The beam of pulse dye laser of the present invention preferably has pulse width range of about 0.1 ms to about 1.5 ms. The fluence of the laser 12 may extend from a range of about 2 J/cm$^2$ to about 12 J/cm$^2$. As shown in FIGS. 1 and 2A, such a laser pulse 20 is intended to coagulate blood vessels 24 in their initial formation stage to reduce fibroblast activity. Such reduction in fibroblast activity will minimize collagen formation to permit the injury or surgical site to have a more normal looking skin.

The method of operating the pulse dye laser generator in accordance with the principles of the present invention includes the application of a preferred range of the optical laser radiation 20 of 575 nm to 600 nm, with a preferred pulse width range of 0.1 ms to 1.5 ms, preferably applied to the patient "P" between two days after the injury or surgical procedure has taken place, and before two months of that date of injury or surgical procedure. By coagulating the blood vessels 24 in their formation stage, which vessels then are typically smaller than 0.1 mm, the formation of collagen may be minimized and thus scar formation is also minimized or prevented. Additional treatment of the surgical site of injury may be provided by the pulse dye laser 12 at follow-up intervals, preferable within that two day to two month time period from the first treatment. FIG. 2A shows a side view of a surgical or wound site on a patient "P", with cellular debris in the wound. FIG. 2B shows that wound site with a representation of a forming scab with endothelial cells at the side of the wound beginning to divide. FIG. 2C depicts new skin forming under the scab and FIG. 2D depicts the continuing formation of scar tissue. It is during the period depicted by FIGS. 2B through 2D when the optical radiation is preferably performed on the patient "P".

Thus it has been shown that the utilization of the pulse dye laser apparatus 10 generating a laser beam 22 with a preferred range of wave length of from about 575 nm to about 600 nm, with a preferred wave length of about 585 nm, and a pulse width range of about 0.1 ms to about 1.5 ms, with a preferred pulse width of about 0.5 ms and a fluence of about 2 J/cm$^2$ to about 12 J/cm$^2$ within a relatively short time interval after the skin injury, may minimize or prevent any scar tissue formation.

The invention also includes a method for the prevention of a scar on the skin of a patient after the beginning healing of a Wound or surgical site, comprising the steps of providing an optical radiation apparatus 10 with a handpiece 14 communicating therewith, energyzing the optical radiation apparatus 10 to provide a beam of light 20, directing the light beam 20 onto a wound or surgical site 22 after 2 days and before 2 months from the date of injury or surgical procedure, wherein the light beam has a wavelength range of about 530 nm to 1000 nm, and the light beam has a fluence range of form 2 J/cm$^2$ to 12 J/cm$^2$. The method includes the steps of maintaining the wavelength of the light beam at about 585 nm, and maintaining the pulse width to a range of 0.1 ms to 10 ms.

The invention also includes a method for the treating a patient "P" with a wound or surgical site in a pre-scarring condition, comprising the steps of providing an optical radiation apparatus 10 with a handpiece 14 communicating therewith, energyzing the optical radiation apparatus 10 to provide a wound treating beam of light 20, directing the light beam onto a wound or surgical site 22 of the patient "P" after 2 days and before 2 months from the date of injury or surgical procedure, to prevent the occurrence of scar formation at the wound or procedure site. The light beam is preferably a pulsed dye laser beam having a wavelength range of about 530 nm to 1000 nm, and a fluence range of from 2 J/cm$^2$ to 12 J/cm$^2$. The laser beam preferably has a pulse width of about 0.1 ms to 10.0 ms, and a beam size of about 3 mm to about 10 mm. in diameter.

We claim:

1. A method for the prevention of a scar on the skin of a patient after the beginning healing of a wound or surgical site, comprising the steps of:

providing a pulse dye laser apparatus with a laser handpiece communicating therewith;

energyzing said pulse dye laser apparatus to provide a beam of laser light; and directing said pulse dye laser beam onto a wound or surgical site of a patient before 2 months from the date of injury or a surgical procedure on said patient, wherein said pulsed dye laser has a fluence range of from 2 J/cm$^2$ to 12 J/cm$^2$.

2. The method for the prevention of a scar on the skin of a patient as recited in claim 1, wherein said pulse dye laser beam has a wavelength range of about 575 nm to about 600 nm.

3. The method for the prevention of a scar on the skin of a patient as recited in claim 1, wherein said pulse dye laser beam has a wavelength of 585 nm.

4. The method for the prevention of a scar on the skin of a patient as recited in claim 3, wherein said pulsed dye laser beam has a pulse width range of about 0.1 ms to 1.5 ms.

5. The method for the prevention of a scar on the skin of a patient as recited in claim 3, wherein said pulsed dye laser beam has a pulse width of about 0.5 ms.

6. The method for the prevention of a scar on the skin of a patient as recited in claim 1, wherein said pulsed dye laser has a beam size range of about 3 mm to about 10 mm in diameter.

7. A method for the prevention of a scar on the skin of a patient after the beginning healing of a wound or surgical site, comprising the steps of:

providing an optical radiation apparatus with a handpiece communicating therewith;

energyzing said optical radiation apparatus to provide a beam of light;

directing said light beam onto a wound or surgical site before 2 months from the date of injury or surgical procedure, said light beam has a wavelength range of about 530 nm to 1000 nm, said light beam having a fluence range of from 2 J/cm$^2$ to 12 J/cm$^2$.

8. The method for the prevention of a scar on the skin of a patient after the beginning healing of a wound or surgical site as recited in claim 7, including the steps of:

maintaining said wavelength of said light beam at about 585 nm; and maintaining said pulse width to a range of 0.1 ms to 10 ms.

9. A method for the treating a patient with a wound or surgical site in a pre-scarring condition, comprising the steps of:

providing an optical radiation apparatus with a handpiece communicating therewith;

energizing said optical radiation apparatus to provide a wound treating beam of light;

directing said light beam onto a wound or surgical site of said patient before 2 months from the date of injury or surgical procedure, to prevent the occurrence of scar formation at said wound or procedure site; wherein said light beam is a pulsed dye laser beam having a wavelength range of about to 1000 nm, and a fluence range of from 2 J/cm$^2$ to 12 J/cm$^2$.

10. The method for the treating a patient with a wound or surgical site as recited in claim 9, wherein said laser beam has a pulse width of about 0.1 ms to 10.0 ms, and a beam size of about 3 mm to about 10 mm in diameter.

* * * * *